(12) United States Patent
Tanaka et al.

(10) Patent No.: US 12,178,922 B2
(45) Date of Patent: *Dec. 31, 2024

(54) PATCH WITH DMSO IN ADHESIVE LAYER

(71) Applicant: HISAMITSU PHARMACEUTICAL CO., INC., Tosu (JP)

(72) Inventors: Ryo Tanaka, Tsukuba (JP); Hideaki Ohashi, Tsukuba (JP); Naruhide Miyoshi, Tsukuba (JP); Takito Shima, Tsukuba (JP); Naoko Fujita, Tsukuba (JP); Yasunari Michinaka, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/244,552

(22) Filed: Apr. 29, 2021

(65) Prior Publication Data

US 2021/0251913 A1    Aug. 19, 2021

Related U.S. Application Data

(63) Continuation of application No. 16/474,213, filed as application No. PCT/JP2017/046697 on Dec. 26, 2017, now Pat. No. 11,020,356.

(30) Foreign Application Priority Data

Dec. 28, 2016 (JP) ................. 2016-256702

(51) Int. Cl.
| | |
|---|---|
| A61K 9/70 | (2006.01) |
| A61K 31/192 | (2006.01) |
| A61K 31/196 | (2006.01) |
| A61K 31/405 | (2006.01) |
| A61K 47/12 | (2006.01) |
| A61K 47/20 | (2006.01) |
| A61K 47/32 | (2006.01) |

(52) U.S. Cl.
CPC .......... *A61K 9/7061* (2013.01); *A61K 31/192* (2013.01); *A61K 31/196* (2013.01); *A61K 31/405* (2013.01); *A61K 47/12* (2013.01); *A61K 47/20* (2013.01); *A61K 47/32* (2013.01)

(58) Field of Classification Search
CPC ..... A61K 9/0014; A61K 47/20; A61K 9/7053
See application file for complete search history.

(56) References Cited

U.S. PATENT DOCUMENTS

| | | |
|---|---|---|
| 4,421,737 A | 12/1983 | Ito et al. |
| 4,695,465 A | 9/1987 | Kigasawa et al. |
| 4,738,848 A | 4/1988 | Yoshida et al. |
| 5,120,545 A | 6/1992 | Ledger et al. |
| 5,208,035 A | 5/1993 | Okuyama et al. |
| 5,776,484 A | 7/1998 | Sasaki et al. |
| 5,869,087 A | 2/1999 | Hirano et al. |
| 5,914,322 A | 6/1999 | Falk et al. |
| 5,916,587 A | 6/1999 | Min et al. |
| 5,945,125 A | 8/1999 | Kim |
| 6,086,911 A | 7/2000 | Godbey |
| 6,262,121 B1 | 7/2001 | Kawaji et al. |
| 6,451,339 B2 | 9/2002 | Patel et al. |
| 6,455,067 B1 | 9/2002 | Woo et al. |
| 6,616,941 B1 | 9/2003 | Seo et al. |
| 9,308,187 B2* | 4/2016 | Hatanaka ............. A61K 31/196 |
| 2002/0106401 A1 | 8/2002 | Hori et al. |
| 2003/0149383 A1 | 8/2003 | Ikeura et al. |
| 2003/0175331 A1 | 9/2003 | Sasaki et al. |
| 2004/0092696 A1* | 5/2004 | Vedula ................... D06N 3/146 |
| | | 428/423.1 |
| 2004/0146548 A1 | 7/2004 | Takada et al. |
| 2005/0129748 A1 | 6/2005 | Takada et al. |
| 2006/0093656 A1 | 5/2006 | Muta et al. |
| 2006/0200063 A1 | 9/2006 | Munro et al. |
| 2006/0234581 A1 | 10/2006 | Saito et al. |
| 2007/0148218 A1 | 6/2007 | Gordon et al. |
| 2009/0074844 A1* | 3/2009 | Nishiura ................... A61P 7/00 |
| | | 514/530 |
| 2012/0071808 A1 | 3/2012 | Sato et al. |
| 2012/0089104 A1* | 4/2012 | Wang ..................... A61P 31/12 |
| | | 604/290 |
| 2012/0215186 A1 | 8/2012 | Kydonieus et al. |
| 2012/0283671 A1 | 11/2012 | Shibata et al. |

(Continued)

FOREIGN PATENT DOCUMENTS

| | | |
|---|---|---|
| CA | 1144070 | 4/1983 |
| CA | 2200068 A1 | 9/1995 |

(Continued)

OTHER PUBLICATIONS

Xu (Scientific Reports, Apr. 2016, vol. 6, pp. 1-12) (Year: 2016).*
Taiwanese Office Action dated Mar. 3, 2021 corresponding to Patent Application No. 106146207.
Japanese Office Action dated Feb. 2, 2021 corresponding to Application No. P2018-559525.
Korean Office Action dated Oct. 16, 2020 corresponding to application No. 10-2019-7017157.
International Preliminary Report on Patentability dated Jul. 11, 2019 corresponding to application No. PCT/JP2017/046697.

(Continued)

*Primary Examiner* — Mark V Stevens (74) *Attorney, Agent, or Firm* — Nath, Goldberg & Meyer; Joshua. B . . . Goldberg (57) ABSTRACT

The patch of the present invention comprises a backing layer and an adhesive layer laminated on the backing layer, wherein a water vapor transmission rate of the backing layer is 400 g/m²·24 hours or more, and the adhesive layer comprises a drug, dimethylsulfoxide and an adhesive. Such a patch does not fall off easily even after long wear.

14 Claims, 2 Drawing Sheets

(56) References Cited

U.S. PATENT DOCUMENTS

| | | | |
|---|---|---|---|
| 2013/0211351 A1* | 8/2013 | Fuhrherr | A61K 31/407 604/307 |
| 2015/0202171 A1* | 7/2015 | Hatanaka | A61K 9/7038 514/567 |
| 2015/0224063 A1 | 8/2015 | Ogino et al. | |
| 2015/0297507 A1 | 10/2015 | Grenier et al. | |
| 2017/0348246 A1 | 12/2017 | Tohara et al. | |
| 2019/0350874 A1 | 11/2019 | Tanaka et al. | |
| 2019/0374481 A1 | 12/2019 | Nardi et al. | |
| 2019/0388360 A1 | 12/2019 | Nardi et al. | |

FOREIGN PATENT DOCUMENTS

| | | |
|---|---|---|
| CA | 2380128 A1 | 12/2001 |
| CA | 22000068 C | 1/2005 |
| CN | 1111987 A | 11/1995 |
| CN | 1462187 A | 12/2003 |
| CN | 1489996 A | 4/2004 |
| CN | 1628634 A | 6/2005 |
| CN | 1705472 A | 12/2005 |
| CN | 101442993 A | 5/2009 |
| CN | 101530401 A | 9/2009 |
| CN | 101932329 A | 12/2010 |
| CN | 102448449 A | 5/2012 |
| CN | 103893156 A | 7/2014 |
| CN | 104379139 A | 2/2015 |
| CN | 103933481 B | 4/2016 |
| CN | 105949701 A | 9/2016 |
| CN | 106619580 A | 5/2017 |
| CN | 106999343 A | 8/2017 |
| CN | 107429036 A | 12/2017 |
| CN | 110114064 A | 8/2019 |
| DE | 10049225 A1 | 4/2002 |
| EP | 0524582 A1 | 7/1992 |
| EP | 0950408 A1 | 10/1999 |
| EP | 0997144 A1 | 5/2000 |
| EP | 1400240 A1 | 3/2004 |
| EP | 1477164 A1 | 11/2004 |
| EP | 2196197 A1 | 6/2010 |
| EP | 2370067 B1 | 11/2013 |
| EP | 2865378 A1 | 4/2015 |
| EP | 3563840 A1 | 11/2019 |
| GB | 20445618 A | 2/1980 |
| GB | 2045618 A | 11/1980 |
| GB | 2073588 A | 3/1981 |
| JP | 8026985 A | 5/1985 |
| JP | 861233077 A | 10/1986 |
| JP | S61223077 A | 10/1986 |
| JP | S61-280426 A | 12/1986 |
| JP | S62-181226 A | 8/1987 |
| JP | 63246326 A | 10/1988 |
| JP | 4103528 A | 4/1992 |
| JP | 5155762 A | 6/1993 |
| JP | H05201879 A | 8/1993 |
| JP | 6024969 A | 2/1994 |
| JP | 16-219940 A | 8/1994 |
| JP | H8-500365 A | 1/1996 |
| JP | H09208460 A | 8/1997 |
| JP | 9315957 A | 12/1997 |
| JP | 10182450 A | 7/1998 |
| JP | H10182450 A | 7/1998 |
| JP | 2816765 B2 | 8/1998 |
| JP | 10218793 A | 8/1998 |
| JP | 1035458 A | 2/1999 |
| JP | H11255644 A | 9/1999 |
| JP | 11322590 A | 11/1999 |
| JP | H11-322595 A | 11/1999 |
| JP | 2001058961 A | 3/2001 |
| JP | 2001233769 A | 8/2001 |
| JP | 2001302502 A | 10/2001 |
| JP | 2002020274 A | 1/2002 |
| JP | 2002193793 A | 7/2002 |
| JP | 2002226366 A | 8/2002 |
| JP | 2002-338462 A | 11/2002 |
| JP | 2003-063955 A | 3/2003 |
| JP | 2003-319967 A | 11/2003 |
| JP | 2006-206454 A | 8/2006 |
| JP | 2006288887 A | 10/2006 |
| JP | 200715963 A | 1/2007 |
| JP | 2007-511605 A | 5/2007 |
| JP | 2008-508954 A | 3/2008 |
| JP | 2011162514 A | 8/2011 |
| JP | 5075378 B2 | 8/2012 |
| JP | 2013-184977 A | 9/2013 |
| JP | 2013-535438 A | 9/2013 |
| JP | 2014148582 A1 | 9/2014 |
| JP | 2015-522049 A | 8/2015 |
| JP | 2016-222631 A | 12/2016 |
| JP | 2019-107220 A | 7/2019 |
| JP | 6744511 B1 | 8/2020 |
| KR | 100191062 B1 | 6/1999 |
| KR | 20000068581 A | 11/2000 |
| KR | 20150023758 A | 3/2015 |
| KR | 1020150023758 A | 3/2015 |
| KR | 2002-0012978 A | 2/2022 |
| NO | 2014181840 A1 | 11/2014 |
| TW | 201406411 A | 2/2014 |
| TW | 1592169 B | 7/2017 |
| TW | 201828931 A | 8/2018 |
| TW | 202139988 A | 11/2021 |
| TW | 202139989 A | 11/2021 |
| TW | 202139990 A | 11/2021 |
| WO | 9608245 A1 | 3/1996 |
| WO | 9954422 A1 | 10/1999 |
| WO | 0178690 A1 | 10/2001 |
| WO | 02094257 A1 | 11/2002 |
| WO | 2004058232 A1 | 7/2004 |
| WO | WO-2005123046 A1 * | 12/2005 ............ A61K 47/18 |
| WO | 2006017807 A2 | 2/2006 |
| WO | 2009096315 A1 | 8/2009 |
| WO | 2009102933 A1 | 8/2009 |
| WO | 2010137699 A1 | 12/2010 |
| WO | 2011/083787 A1 | 7/2011 |
| WO | 2011136330 A1 | 11/2011 |
| WO | 2012009262 A2 | 1/2012 |
| WO | 2012/022837 A1 | 2/2012 |
| WO | 2013191128 A1 | 12/2013 |
| WO | 2014134073 A1 | 9/2014 |
| WO | 2014148582 A1 | 9/2014 |
| WO | 2015/105101 A1 | 7/2015 |
| WO | 2018070370 A1 | 4/2018 |
| WO | 2018124089 A1 | 7/2018 |
| WO | 2018141661 A1 | 8/2018 |
| WO | 2018141662 A1 | 8/2018 |

OTHER PUBLICATIONS

Office Action dated Dec. 17, 2019 corresponding to Taiwanese application No. 106146207.
Extended European Search Report dated Jun. 29, 2020 corresponding to application No. 17887366.7-1109.
Taiwan Office Action dated Aug. 22, 2022 corresponding to TW Patent Application No. 110104894.
Taiwanese Office Action dated Aug. 16, 2022 corresponding to application No. 110104895.
"Office Action dated Feb. 18, 2015 in Japanese Patent Application No. 2014-521452 (with partial English language translation)".
"International Search Report dated Sep. 3, 2013 in PCT/JP2013/066574".
"International Preliminary Report on Patentability and Written Opinion dated Dec. 31, 2014 in PCT/JP2013/066574".
"Philip Fuller, et al., "Diclofenac sodium topical solution with dimethyl sulfoxide, a viable alternative to oral nonsteroidal antiinflammatories in osteoarthritis: review of current evidence", Journal of Multidisciplinary Healthcare, Abstract, vol. 4, 2011,p. 223-231".
"Rajesh Dubey, et al., "Ketorolac Tromethamine Transdermal Gel:Development, In Vitro and In Vivo Evaluation", J. Pain Palliat, Care Pharmacother, vol. 23, No. 1, 2009, pp. 26-34".
"Office Action in Korean Application No. 10-2015-7000960 dated Feb. 8, 2019".

(56) References Cited

OTHER PUBLICATIONS

"Taiwanese Office Action dated Nov. 21, 2016 in corr. Taiwanese Patent Application No. 102122030".
"Hewitt, P.G., et al., "In Vitro Cutaneous Disposition of a Topical Diclofenac Lotion in Human Skin: Effect of a Multi- Dose Regimen", Pharmaceutical Research, vol. 15, No. 7, Jul. 1998, pp. 988-992".
"Extended European Search Report dated Feb. 3, 2016 in Application No. 13807634.4".
"Adhesive compn. for low polar plastic resins-comprises an alky(meth)acrylate copolymer, and tackifier comprising rosin and hydrogenerated petroleum resin" DERWENT, Jan. 27, 1995, xp002216523, two pages.
Supplemental Extended European Search Report dated Aug. 16, 2010 corresponding to application No. 03706968.9.
Canadian Office Action dated Oct. 22, 2010 corresponding to application No. 2519195.
Chinese Notification of the First Action dated Oct. 13, 2006 corresponding to application No. 200480007150.X.
Notice of Rejection dated May 11, 2007 corresponding to Chinese application No. 200480007150.X.
Machine Translation of JP2001-302502.
Communication Pursuant to Article 94(3)EPC dated Dec. 27, 2010 corresponding to application No. 04712660.1.
Korean Office Action dated Nov. 5, 2010 corresponding to application 10-2005-701273.
Rakool Pharmaceutical Marketing Co., Ltd. , "Package insert for- "Rakool" Diclofenac Na PAP 70mg, 140mg, 280mg ", 2006.
International Search Report dated Apr. 26, 2022 corresponding to application No. PCT/JP2022/007229.
"Diclonac Na PAP 70mg Rakool"; 2014.
"Clinical Effect of Diclofenac Sodium Tape Formulation (Voltaren Tape) on Pain Disease"; Therapeutic Research; vol. 26, No. 12; 2005.
Matsunaga, et al. "Clinical Experience of Diclofenac Sodium Cream on Osteoarthritis of the Knee and Rheumatoid Arthritis"; vol. 11, No. 8; Aug. 1983.
A Comparative Study of Diclofenac Sodium Percutaneous Agent (TP318) and its Base Preparation in Treating Osteoarthrosis of the Knee Conclusion; 2000.
International Preliminary Report on Patentability(IPRP) dated Aug. 25, 2022 corresponding to application No. PCT/JP2021/004740.
International Preliminary Report on Patentability(IPRP) dated Aug. 25, 2022 corresponding to application No. PCT/JP2021/004819.
International Preliminary Report on Patentability(IPRP) dated Aug. 25, 2022 corresponding to application No. PCT/JP2021/004741.
Office Action dated Aug. 17, 2022 corresponding to U.S. Appl. No. 17/184,797.
Chinese Office Action dated Mar. 2, 2022 corresponding to application No. 201780080620.2.
Final Office Action dated Mar. 13, 2023 corresponding to U.S. Appl. No. 17/184,797.
Simon, LS et al. , "Efficacy and safety of topical diclofenac containing dimethyl sulfoxide (DMSO) compared with DMSO those of topical placebo, DMSO vehicle and oral diclofenac for knee osteoarthritis: PAIN", vol. 143, Issue 3, https://doi.org/10.1016/j.pain.2009.03.008, Jun. 2009, p. 238-p. 245.
Office Action dated Apr. 25, 2023 corresponding to BR Patent Application No. BR112021016517-7.
Office Action dated Jun. 10, 2023 corresponding to Chinese application No. 202180013224.4.
Office Action dated Jul. 29, 2023 corresponding to CN Patent Application No. 202080016834.5.
International Preliminary Report on Patentability dated Aug. 25, 2021corresponding to application No. PCT/JP2020/007182.
Xu, et al. "Controlled Water Vapor Transmission Rate Promotes Wound-Healing Via Wound Re-Epithelialization and Contraction Enhancement"; Scientific Reports; Apr. 18, 2016.
"Tie Da Ning PAP DS"; Dec. 30, 2015.
Mckay et al., "The Influence of Styrene-Butadiene Diblock Copolymer on Styrene-Butadiene-Styrene Triblock Copolymer Viscoelastic Properties and Product Performance", Journal of Applied Polymer Science vol. 56, Iss. 8, May 23, 1995, p. 947-p958.

\* cited by examiner

PATCH WITH DMSO IN ADHESIVE LAYER

This is a Continuation Application of U.S. patent application Ser. No. 16/474,213, filed Jun. 27, 2019, an application filed as a national stage under 371 of Application No. PCT/JP2017/046697 filed Dec. 26, 2017 and claiming benefit from Japanese Application No. 2016-256702, filed Dec. 28, 2016, the content of each of which is hereby incorporated by reference in its entirety.

TECHNICAL FIELD

The present invention relates to a patch.

BACKGROUND ART

Dimethyl sulfoxide (DMSO) is used in a formulation to dissolve a drug therein. For example, Patent Literature 1 discloses a patch of diclofenac sodium having DMSO used as a solubilizing agent.

CITATION LIST

Patent Literature

Patent Literature 1: International Publication No. WO 2013/191128

SUMMARY OF INVENTION

Technical Problem

The adhesiveness of the patch generally decreases gradually with time. The present inventors have found that when DMSO is blended in an adhesive layer of a patch, a composition which gives tackiness to the patch is plasticized, resulting in a decrease in tackiness of the adhesive layer. The present inventors have also found that when the patch comprising DMSO is worn for a long time (such as 24 hours), sufficient adhesiveness may not last till the end and so the patch may fall off before treatment is completed.

Solution to Problem

The present inventors have found that by combining an adhesive layer comprising DMSO with a backing having a particular water vapor transmission rate, the adhesiveness of a patch after long wear is greatly improved, and thus have completed the present invention.

A patch of the present invention comprises: a backing layer and an adhesive layer laminated on the backing layer, wherein a water vapor transmission rate of the backing layer is 400 g/m²·24 hours or more, and the adhesive layer comprises a drug, DMSO and an adhesive.

The water vapor transmission rate of the backing layer may be 750 g/m²·24 hours or more, or may be 2000 g/m²·24 hours or more.

The adhesive layer may comprise at least one adhesive selected from a rubber adhesive, an acrylic adhesive and a silicone adhesive, and may comprise a styrene-isoprene-styrene block copolymer.

The drug may be one or more drugs selected from the group consisting of ketoprofen, diclofenac sodium and indomethacin. In addition, the adhesive layer may comprise an organic acid.

Advantageous Effects of Invention

According to the patch of the present invention, by using a backing layer having a high water vapor transmission rate, sufficient adhesiveness is maintained for a long time. Thus, the patch does not fall off easily even after long wear (such as 24 hours). As a result, when the drug is a drug with analgesic and anti-inflammatory effects such as ketoprofen, diclofenac sodium or indomethacin, a sufficient cumulative skin permeation amount of the drug can be achieved more surely after the patch is worn on the skin of a patient for 24 hours. In addition, the maximum plasma concentration (Cmax) of the drug is achieved more surely. Therefore, according to the patch of the present invention, more effective drug treatment is possible.

DESCRIPTION OF EMBODIMENTS

A patch of the present invention comprises a backing layer and an adhesive layer laminated on the backing layer. The adhesive layer is usually laminated on one side of the backing layer, and a peelable film is laminated on the other side of the adhesive layer as needed.

First, the adhesive layer will be described. The adhesive layer is a part that sticks to the skin when the patch is worn, and comprises at least a drug, DMSO and an adhesive.

The drug is a component soluble in DMSO. The drug may be a drug with analgesic and anti-inflammatory effects such as loxoprofen, felbinac, flurbiprofen, indomethacin, ketoprofen and diclofenac sodium, or may be an analgesic drug or narcotic drug such as buprenorphine, fentanyl and butorphanol, or other drugs such as clonidine, estradiol, tulobuterol or oxybutynin. The content of the drug is, for example, 1% by mass to 20% by mass or 2% by mass to 10% by mass based on the total mass of the adhesive layer.

DMSO dissolves the drug to improve the skin permeability of the drug, while it leads to a decrease in tackiness of the adhesive layer. From the viewpoint of balancing these, the content of DMSO is preferably 1% by mass to 20% by mass, more preferably 1% by mass to 15% by mass, further preferably 2% by mass to 10% by mass, and particularly preferably 3% by mass to 10% by mass, based on the total mass of the adhesive layer.

The ratio of the drug to DMSO varies depending on drugs, and for example, when diclofenac sodium is contained as a drug, from the viewpoint of improving the skin permeability of diclofenac sodium and preventing diclofenac sodium from crystallizing, the ratio of the mass of diclofenac sodium to the mass of DMSO in the adhesive layer in the patch just before application is preferably 1:0.3 to 1:4, more preferably 1:0.4 to 1:3, further preferably 1:0.6 to 1:3, and particularly preferably 1:0.72 to 1:3.

The adhesive layer may comprise at least one adhesive selected from a rubber adhesive, an acrylic adhesive and a silicone adhesive. The rubber adhesive is, for example, polyisoprene, polyisobutylene (PIB), polybutadiene, a styrene-butadiene-styrene block copolymer, a styrene-isoprene-styrene (SIS) block copolymer, a styrene-butadiene rubber, a styrene-isoprene rubber, or a combination thereof.

From the viewpoint of enhancing the skin permeability of the drug and enhancing the tackiness of the patch, among them, an SIS block copolymer, PIB or a combination thereof is preferable, and a mixture of an SIS block copolymer and PIB is more preferable. The acrylic adhesive is, for example, an adhesive obtained by polymerizing or copolymerizing at least one (meth)acrylic monomer such as (meth)acrylic acid, 2-ethylhexyl (meth)acrylate, methyl (meth)acrylate, butyl (meth)acrylate or hydroxyethyl (meth)acrylate. The silicone adhesive comprises, as a main component, for example, a silicone rubber such as polydimethylsiloxane, polymethylvinylsiloxane or polymethylphenylsiloxane.

When the adhesive is a rubber adhesive, from the viewpoint of tackiness of the patch, the content of the adhesive may be 10% by mass to 70% by mass, 10% by mass to 40% by mass, 15% by mass to 50% by mass, 15% by mass to 35% by mass, or 30% by mass to 40% by mass, based on the total mass of the adhesive layer. When the adhesive is an acrylic adhesive or silicone adhesive, the content of the adhesive may be 50% by mass to 90% by mass, based on the total mass of the adhesive layer.

The adhesive layer may further comprise an organic acid for the purpose of promoting the transdermal absorption of the drug, preventing the drug from crystallizing with time, or the like. Examples of the organic acid include aliphatic acids such as aliphatic monocarboxylic acids (such as formic acid, acetic acid, propionic acid, butyric acid, isobutyric acid, valeric acid, caproic acid, enanthic acid, caprylic acid, nonanoic acid, capric acid, lauric acid, oleic acid, linoleic acid, linolenic acid, isostearic acid, sorbic acid and pyruvic acid), aliphatic dicarboxylic acids (such as oxalic acid, malonic acid, succinic acid, glutaric acid, adipic acid, sebacic acid, maleic acid, fumaric acid and oxaloacetic acid), and aliphatic tricarboxylic acids (such as aconitic acid and propane tricarboxylic acid); hydroxy acids (such as glycolic acid, lactic acid, tartronic acid, glyceric acid, hydroxybutyric acid, malic acid, tartaric acid, citric acid, isocitric acid, sugar acid, gluconic acid, glucuronic acid, ascorbic acid and erythorbic acid); aromatic carboxylic acids (such as benzoic acid, gallic acid, salicylic acid, acetylsalicylic acid and phthalic acid); other organic acids (such as mesylic acid and besylic acid); or salts thereof (for example, a alkali metal salt such as a sodium salt). When the drug is diclofenac sodium, from the viewpoint of promoting the transdermal absorption of diclofenac sodium and preventing diclofenac sodium from crystallizing out with time, among these organic acids, citric acid, oleic acid, mesylic acid or an alkali metal salt thereof is particularly preferable. By comprising such an organic acid, a sufficient cumulative skin permeation amount of the drug is obtained more surely. These organic acids may be used alone or in combination of two or more thereof. From the viewpoint of improving the skin permeability of the drug and preventing the drug from crystallizing over time, the content of the organic acid may be 0.01% by mass to 20% by mass %, 0.1% by mass to 15% by mass, or 0.2% by mass to 13% by mass, based on the total mass of the adhesive layer.

The adhesive layer may further comprise a tackifier, a plasticizer or other additives. The tackifier is, for example, an alicyclic saturated hydrocarbon resin, a hydrogenated rosin ester, a terpene resin or a combination thereof. The content of the tackifier is, for example, 5% by mass to 60% by mass, 10% by mass to 50% by mass, 25% by mass to 45% by mass, or 30% by mass to 35% by mass, based on the total mass of the adhesive layer. The plasticizer is, for example, a liquid paraffin or a liquid polybutene. The content of the plasticizer is, for example, 7% by mass to 70% by mass, 10% by mass to 60% by mass or 11% by mass to 25% by mass, based on the total mass of the adhesive layer.

The adhesive layer may be a single layer consisting of one composition, or may be a multilayer in which layers having different compositions are laminated. From the viewpoint of properly adhering the patch to the skin, the total thickness of the adhesive layer is preferably 10 μm to 1000 μm and more preferably 30 μm to 300 μm.

The probe tack value of the adhesive layer is preferably 30 gF or more, and more preferably 40 gF or more. The probe tack value of the adhesive layer may be, for example, 43 gF or more, 44 gF or more, 53 gF or more, 61 gF or more, 68 gF or more, or 71 gF or more. The higher the probe tack value is, the more the adhesiveness of the patch is improved. From the viewpoint of reducing skin irritation, the probe tack value may be 2000 gF or less, 1500 gF or less, or 1000 gF or less. In the present specification, the probe tack value of the adhesive layer is measured in accordance with the probe tack test method of ASTM D2979.

Next, the backing layer will be described. The backing layer holds the adhesive layer. The water vapor transmission rate of the backing layer is 400 g/m$^2$·24 hours or more. When the backing layer having such a high water vapor transmission rate is used, DMSO gradually volatilizes from the patch worn on the skin, so that the tackiness of the patch improves and the patch does not fall off easily even after long wear. Although the water vapor transmission rate is originally an indicator for the transmission of water, the present inventors have found that the backing having a high water vapor transmission rate also has a high transmission (volatility) of DMSO. The water vapor transmission rate of the backing layer may be, for example, 422 g/m$^2$·24 hours or more, 750 g/m$^2$·24 hours or more, 2000 g/m$^2$·24 hours or more, 2077 g/m$^2$·24 hours or more, 4000 g/m$^2$·24 hours or more, 5500 g/m$^2$·24 hours or more, 5667 g/m$^2$·24 hours or more, or 8408 g/m$^2$·24 hours or more. The upper limit of the water vapor transmission rate may be 20000 g/m$^2$·24 hours. The water vapor transmission rate of the backing layer in such a range is more effective for improving the tackiness of the patch since DMSO volatilizes from the adhesive layer more easily.

The water vapor transmission rate of the backing layer in the present invention refers to the water vapor transmission rate at 40° C. as defined in JIS Z0208: 1976 (water vapor transmission rate test method (cup method) of moisture-proof packaging material).

It is preferable that the backing layer is a monolayer or a laminate of a fabric (a woven fabric, a nonwoven fabric or knitted fabric) made of fibers, or a nonporous or porous film (sheet). A material of the backing layer is preferably one or more materials selected from polyester (such as polyethylene terephthalate (PET), polyethylene isophthalate, polypropylene terephthalate, polypropylene isophthalate, polybutylene terephthalate or polyethylene naphthalate), polyolefin (a polymer or copolymer of a vinyl monomer such as ethylene, propylene, vinyl acetate or acrylonitrile), polyamide (such as nylon or silk), polyurethane (PU), or cellulose (such as cotton or hemp). The fabric (a woven fabric, a nonwoven fabric or knitted fabric) may be coated with a rubber composition. The rubber composition comprises a rubber adhesive. The rubber adhesive is, for example, polyisoprene, PIB, polybutadiene, a styrene-butadiene-styrene block copolymer, an SIS block copolymer, a styrene-butadiene rubber, a styrene-isoprene rubber, or a combination thereof. The rubber composition may comprise a tackifier. The tackifier is, for example, an alicyclic saturated hydrocarbon resin, a hydrogenated rosin ester, a terpene resin, or a combination thereof. The rubber compositions may further comprise an additive such as a plasticizer or a filler. The thickness of the backing layer is, for example, 0.1 mm to 2 mm. The basis weight of the backing layer is, for example, 30 g/m² to 200 g/m². In the present specification, the thickness and basis weight of the backing layer are measured in accordance with JIS L 1906: 2000.

When the backing layer is a fabric, it is preferable that the 50% modulus (JIS L 1018: 1999) in both the longitudinal direction (direction of material flow) and the transverse direction (width direction of material) of the backing layer is 1 N/50 mm to 12 N/50 mm. When the 50% modulus is 12 N/50 mm or less, the stress applied to the patch due to stretching of the skin is lower, and the adhesiveness to the skin thus is better.

When the backing layer is a film, the material is preferably a material having a high water vapor transmission (high DMSO transmission) such as polyurethane. The film made of polyurethane is excellent in stretchability and therefore preferable from the viewpoint of enhancing adhesiveness and conformability of the patch to the skin.

It is preferable that the backing layer is, for example, a nonwoven fabric or film made of polyurethane, a knit fabric made of polyethylene terephthalate, a polyester fabric coated with a rubber composition, or a combination thereof. More specifically, it is preferable that the backing layer is a laminate of a film made of polyurethane and a nonwoven fabric made of polyurethane fibers, a nonwoven fabric made of PET fibers, or a polyester fabric coated with a rubber composition.

From the viewpoint of preventing the drug from crystallizing in a unused patch, the DMSO concentration in the patch just before application may be, for example, 1% by mass to 20% by mass, 2% by mass to 12% by mass, 2% by mass to 10% by mass, or 2% by mass to 8% by mass, based on the total mass of the adhesive layer. In addition, DMSO concentration in the patch after 24 hours of wear is preferably 0.1% by mass to 4% by mass, and more preferably 0.1% by mass to 1.5% by mass. It is preferable that the backing layer is one capable of achieving such a decrease in the DMSO concentration. More specifically, when the DMSO concentration in the patch just before application is 2% by mass to 8% by mass, a backing layer in which the decrease rate of the DMSO concentration is 0.08% by mass/hour to 0.16% by mass/hour (that is, a decrease of 1.92% by mass to 3.84% by mass per 24 hours) is preferable. From another viewpoint, when the DMSO concentration in the patch just before application is 2% by mass to 8% by mass, the backing layer in which the half-life of the DMSO concentration is 5 hours to 24 hours is preferable. A backing layer satisfying such a condition tends to maintain sufficient adhesiveness even after worn for 24 hours. Both the decrease rate and the half-life of the DMSO concentration in the patch as described are calculated by placing the patch with the backing layer facing upward under the conditions of 30° C. and 65% RH and measuring the change in the DMSO concentration in the patch by gas chromatography (GC).

The patch may be prepared, for example, by the following method without being limited thereto, and may be prepared by using any known method. First, components constituting an adhesive layer are mixed with each other at a predetermined ratio to obtain a mixture having the components homogeneously dissolved therein. Next, the mixture is spread on a peelable film (release film or release liner) at a predetermined thickness to form an adhesive layer. Then, a backing layer is contact bonded to the adhesive layer with the adhesive layer sandwiched between the release liner and the backing layer. Finally, it may be cut into a desired shape to obtain the patch. In this case, the release liner is removed at the time of applying the patch.

EXAMPLES (Preparation of Patch)
In the following examples, unless otherwise stated, a patch was prepared as follows:
1) Components of an adhesive layer were mixed with each other and spread on a release film (PET film which had been subjected to release treatment). This was dried to remove DMSO to a predetermined amount and form the adhesive layer (100 g/m²) having a thickness of 100 μm.
2) A backing layer was laminated on the adhesive layer to obtain a patch. The patch was cut into pieces having a suitable size as appropriate.

(Measurement of Water Vapor Transmission Rate of Backing Layer)
In the following examples, the water vapor transmission rate of the backing layer used was measured under the conditions of 40° C. and 90% RH in accordance with JIS Z0208.

(Evaluation of Tackiness of Patch)
In the following examples, unless otherwise stated, the tackiness of a patch was evaluated by the 180° peel test described below:
1) A test piece of 1 cm×5 cm was prepared from the patch and stored under predetermined conditions for a predetermined time.
2) A release film was removed from the test piece, and the test piece was applied on a stainless steel plate.
3) Using an Instron type tensile tester, the test piece was peeled off from the stainless steel plate in the direction of 180° at a rate of 30 cm/min, and the peel strength (gF/cm) was measured.
4) The average peel strength (gF/cm) was calculated from the integrated value of the measured peel strength in a section showing steady peeling. A high peel strength represents excellent tackiness.

(Evaluation of Adhesiveness of Patch)
In the following examples, the adhesiveness of a patch to the skin was evaluated by the following method. The patch was applied to the skin of the subject. After 24 hours, the degree of adherence of the patch was visually observed. The patch was rated as "A" when 90% or more of its area adhered to the skin, and as "B" when it was otherwise.

Test Example 1

Patches (placebo patches) having the compositions shown in Table 1 were prepared. In the table, "PET film", "PET film/PET nonwoven fabric", "PU film/PU nonwoven fabric" and "PET knitted fabric" refer to a film made of PET, a laminate of a film made of PET and a nonwoven fabric made of PET fibers, a laminate of a film of PU and a nonwoven fabric made of PU fibers, and a knitted fabric made of PET, respectively. The rubber adhesive in Table 1 is a mixture of an SIS block copolymer and PIB and comprises the SIS block copolymer and PIB in a mass ratio of 19:7. As "PET knitted fabric", one having a water vapor transmission rate of 5667 g/m²·24 hours, a 50% modulus in the longitudinal direction of 3.9 N/50 mm and a 50% modulus in the transverse direction of 3.4 N/50 mm was used (the same applies to the following examples). The patch was placed in an incubator at 30° C. and 65% RH with a backing layer facing upward and a release film facing downward, and stored. After 24 hours, DMSO was extracted from the patch and quantified by GC. The storage conditions are conditions simulating the environment when the patch is worn on skin for 24 hours.

Figure 1:
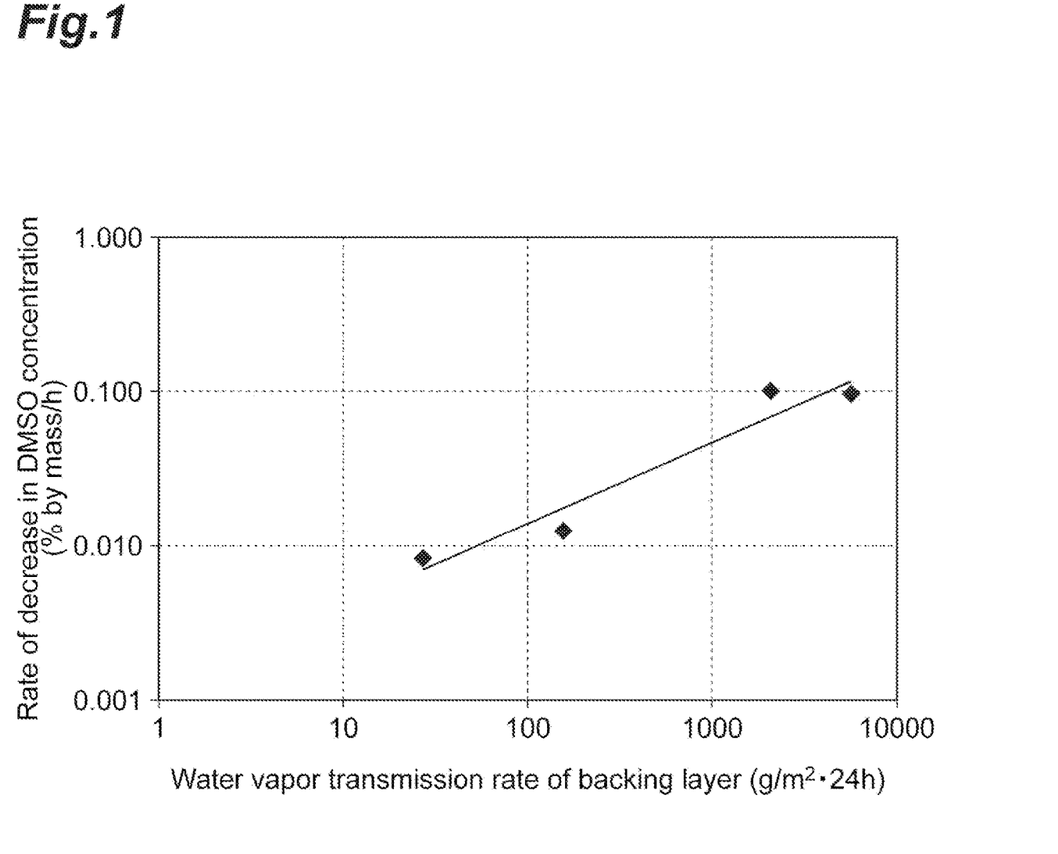
FIG. 1 is a graph showing the relationship between the water vapor transmission rate of the backing layer and the rate of decrease in the concentration in % by mass of DMSO (hereinafter referred to "DMSO concentration") based on the total mass of the adhesive layer (Test Example 1).
Figure 2:
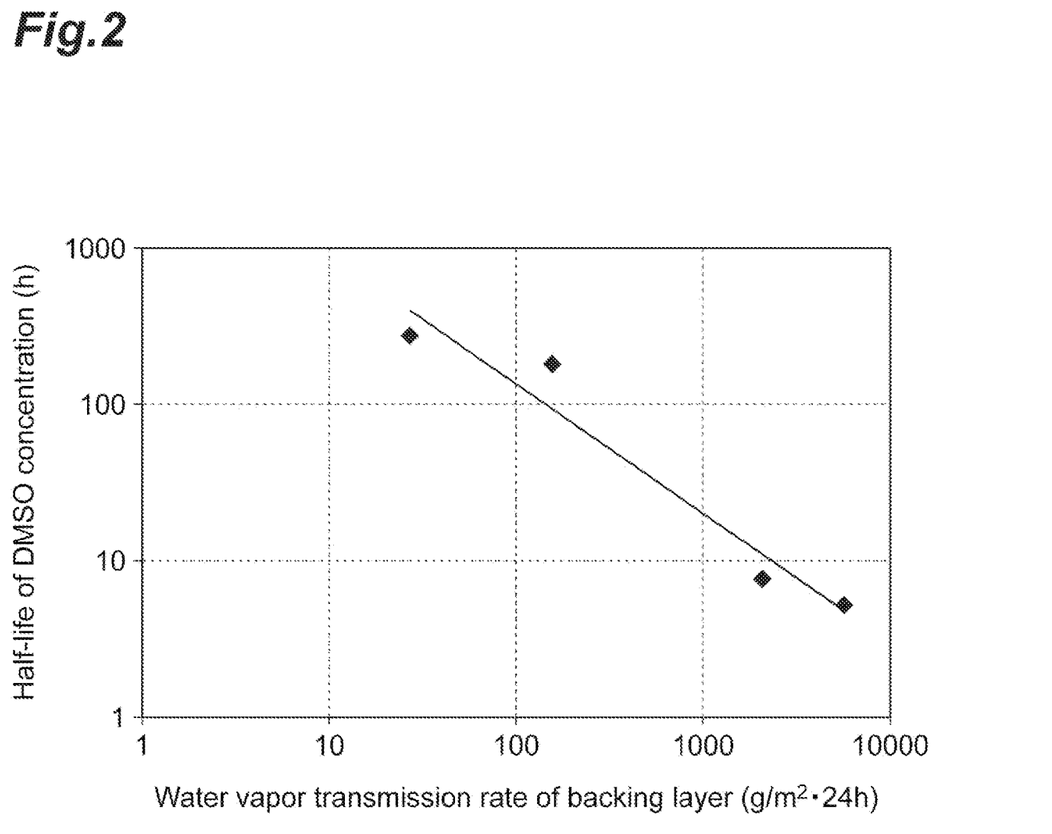
FIG. 2 is a graph showing the relationship between the water vapor transmission rate of the backing layer and the half-life of the concentration in % by mass of DMSO based on the total mass of the adhesive layer (Test Example 1).

The results are shown in Table 1, FIG. 1 and FIG. 2. Compared to the patches of Reference Examples 1 and 2 each having a backing layer with the water vapor transmission rate of less than 400 g/m²·24 hours, decrease in DMSO concentration after storing for 24 hours was much greater with the patches of Reference Examples 3 and 4 each having a backing layer with the water vapor transmission rate of 400 g/m²·24 hours or more. There was observed such a relationship as the patch having a backing layer with a high water vapor transmission rate was high in the decrease rate of the DMSO concentration in the adhesive layer (FIG. 1) and short in the half-life of the DMSO concentration (FIG. 2).

The tackiness of each of patches stored under the same conditions for 24 hours was also evaluated. The results are shown in Table 1. The patches of Reference Examples 3 and 4 each having a backing layer with the water vapor transmission rate of 400 g/m²·24 hours or more were better in tackiness (peel strength) after stored for 24 hours, as compared with the patches of Reference Examples 1 and 2 each having a backing layer with the water vapor transmission rate of less than 400 g/m²·24 hours.

Furthermore, patches having the compositions shown in Table 1 were evaluated for the adhesiveness after 24 hours. The results are shown in Table 1. The patches of Reference Examples 3 and 4 each having a backing layer with the water vapor transmission rate of 400 g/m²·24 hours or more were good in adhesiveness after worn for 24 hours.

Test Example 2

Patches having the compositions shown in Table 2 were prepared. The rubber adhesive in Table 2 is a mixture of an SIS block copolymer and PIB and comprises the SIS block copolymer and PIB in a mass ratio of 19:7. The tackiness of each of the patches of Examples 2 and 7 to 9 was evaluated by the probe tack value measured under the following conditions in accordance with the probe tack test method of ASTM D2979. A high prove tack value represents excellent tackiness.

Tester: Tacking tester (RHESCA Co., LTD.)
Material of the tip of probe part: stainless steel
Diameter of the adhesive face: 5 mm
Detaching rate: 2 mm/s
Adhesion load: 200 gF/cm²
Adhesion time: 1 second In addition, one each of patches of Examples 1 to 15 and Comparative Examples 1 to 3 was applied to a healthy adult male on his lower back, and the adhesiveness after 24 hours was evaluated. The results are shown in Table 2. The patches of Examples 1 to 15 each having a backing layer with the water vapor transmission rate of 400 g/m²·24 hours or more were good in adhesiveness after worn for 24 hours.

In addition, a patch of Example 2 was placed in an incubator at 30° C. and 65% RH with a backing layer facing upward, and stored. After 24 hours, the DMSO concentration (% by mass) in the adhesive layer was quantified by GC and the change in the DMSO concentration was examined. The DMSO concentration after 24 hours was 1.2% by mass based on the total mass of the adhesive layer, which corresponds to 33% based on 100% of the initial (before storage) DMSO concentration. The decrease rate of the DMSO concentration and the half-life of the DMSO concentration calculated from the change in the DMSO concentration was 0.1% by mass/hour and 15 hours, respectively.

TABLE 1

|  |  | Reference Example 1 | Reference Example 2 | Reference Example 3 | Reference Example 4 |
|---|---|---|---|---|---|
| Adhesive layer | Rubber adhesive (SIS/PIB = 19/7) | 31.3 | 31.3 | 31.6 | 31.7 |
|  | Tackifier resin | 44.6 | 44.6 | 44.9 | 45.1 |
|  | Liquid paraffin | 15.7 | 15.7 | 15.8 | 15.8 |
|  | DMSO | 3.4 | 3.4 | 2.7 | 2.4 |
|  | Others | 5 | 5 | 5 | 5 |
|  | Total (% by mass) | 100 | 100 | 100 | 100 |
| Backing layer | Material | PET film | PET film/ PET nonwoven fabric | PU film/ PU nonwoven fabric | PET knitted fabric |
|  | Water vapor transmission rate (g/m² · 24 h) | 27 | 156 | 2077 | 5667 |
|  | Thickness (mm) | — | — | 0.2 | 0.54 |
|  | Basis weight (g/m²) | — | — | 0.05 | 110 |
| Results | DMSO concentration after 24 hours (vs. initial concentration %) | 94 | 91 | 11 | 4.2 |
|  | DMSO concentration after 24 hours (% by mass) | 3.20 | 3.10 | 0.30 | 0.10 |
|  | Rate of decrease in DMSO concentration (% by mass/h) | 0.008 | 0.012 | 0.1 | 0.1 |
|  | Half-life of DMSO concentration (h) | 274 | 180 | 7.6 | 5.2 |
|  | Peel strength after 24 hours (gF/cm) | 3.9 | 4.5 | 459 | 412 |
|  | Adhesiveness after 24 hours of wear | B | B | A | A |

TABLE 2

|  |  | Example 1 | Example 2 | Example 3 | Example 4 | Example 5 | Example 6 |
|---|---|---|---|---|---|---|---|
| Adhesive layer | Ketoprofen | 5.0 |  |  | 2.0 |  |  |
|  | Diclofenac sodium |  | 5.0 |  |  | 2.0 |  |
|  | Indomethacin |  |  | 5.0 |  |  | 2.0 |
|  | Rubber adhesive | 35.1 | 32.8 | 35.1 | 35.1 | 32.8 | 35.1 |
|  | Tackifier resin | 34.8 | 32.4 | 34.8 | 34.8 | 32.4 | 34.8 |
|  | Liquid paraffin | 16.1 | 15.1 | 16.1 | 22.1 | 21.1 | 22.1 |
|  | DMSO | 2.0 | 7.7 | 2.0 | 2.0 | 7.7 | 2.0 |
|  | Citric acid | 2.0 | 2.0 | 2.0 | 1.0 | 1.0 | 1.0 |
|  | Oleic acid | 5.0 | 5.0 | 5.0 | 3.0 | 3.0 | 3.0 |
|  | Mesylic acid | 0 | 0 | 0 | 0 | 0 | 0 |
|  | Total | 100 | 100 | 100 | 100 | 100 | 100 |
| Backing layer | Material | PET knitted fabric | PET knitted fabric | PET knitted fabric | PET knitted fabric | PET knitted fabric | PET knitted fabric |
|  | Water vapor transmission rate (g/m² · 24 h) | 5667 | 5667 | 5667 | 5667 | 5667 | 5667 |
| Results | Probe tack value just before application (gF) | — | 71.0 | — | — | — | — |
|  | Adhesiveness after 24 hours of wear | A | A | A | A | A | A |

|  |  | Example 7 | Example 8 | Example 9 | Example 10 | Example 11 | Example 12 |
|---|---|---|---|---|---|---|---|
| Adhesive layer | Ketoprofen |  |  |  |  |  |  |
|  | Diclofenac sodium | 5.0 | 5.0 | 5.0 | 5.0 | 5.0 | 5.0 |
|  | Indomethacin |  |  |  |  |  |  |
|  | Rubber adhesive | 34.4 | 35.2 | 35.1 | 35.1 | 35.1 | 35.1 |
|  | Tackifier resin | 34.1 | 34.8 | 34.8 | 34.8 | 34.8 | 34.8 |
|  | Liquid paraffin | 15.8 | 16.2 | 16.1 | 16.1 | 16.1 | 16.1 |
|  | DMSO | 3.6 | 1.8 | 2.0 | 2.0 | 2.0 | 2.0 |
|  | Citric acid | 2.0 | 2.0 | 2.0 | 7.0 | 0 | 0 |
|  | Oleic acid | 5.0 | 5.0 | 5.0 | 0 | 7.0 | 0 |
|  | Mesylic acid | 0 | 0 | 0 | 0 | 0 | 7.0 |
|  | Total | 100 | 100 | 100 | 100 | 100 | 100 |
| Backing layer | Material | PET knitted fabric | PET knitted fabric | PET knitted fabric | PET knitted fabric | PET knitted fabric | PET knitted fabric |
|  | Water vapor transmission rate (g/m² · 24 h) | 5667 | 5667 | 5667 | 5667 | 5667 | 5667 |
| Results | Probe tack value just before application (gF) | 211 | 209 | 216 | — | — | — |
|  | Adhesiveness after 24 hours of wear | A | A | A | A | A | A |

|  |  | Example 13 | Example 14 | Example 15 | Comparative Example 1 | Comparative Example 2 | Comparative Example 3 |
|---|---|---|---|---|---|---|---|
| Adhesive layer | Ketoprofen | 7.0 |  |  | 2.0 |  |  |
|  | Diclofenac sodium |  | 7.0 |  |  | 2.0 |  |
|  | Indomethacin |  |  | 7.0 |  |  | 2.0 |
|  | Rubber adhesive | 35.1 | 32.8 | 35.1 | 35.1 | 32.8 | 35.1 |
|  | Tackifier resin | 34.8 | 32.4 | 34.8 | 34.8 | 32.4 | 34.8 |
|  | Liquid paraffin | 12.1 | 11.1 | 12.1 | 19.1 | 18.1 | 19.1 |
|  | DMSO | 2.0 | 7.7 | 2.0 | 2.0 | 7.7 | 2.0 |
|  | Citric acid | 2.0 | 2.0 | 2.0 | 2.0 | 2.0 | 2.0 |
|  | Oleic acid | 7.0 | 7.0 | 7.0 | 5.0 | 5.0 | 5.0 |
|  | Mesylic acid | 0 | 0 | 0 | 0 | 0 | 0 |
|  | Total | 100 | 100 | 100 | 100 | 100 | 100 |
| Backing layer | Material | PU film/ PU nonwoven fabric | PU film/ PU nonwoven fabric | PU film/ PU nonwoven fabric | PET film | PET film | PET film |
|  | Water vapor transmission rate (g/m² · 24 h) | 2077 | 2077 | 2077 | 27 | 27 | 27 |
| Results | Probe tack value just before application (gF) | — | — | — | — | — | — |
|  | Adhesiveness after 24 hours of wear | A | A | A | B | B | B |

Test Example 3

Patches having the compositions shown in Table 3 were prepared. For each of the patches having the compositions shown in Table 3, the probe tack value was measured in the same manner as in Example 2, and the tackiness was evaluated. The rubber adhesive in Table 3 is a mixture of an SIS block copolymer and PIB and comprises the SIS block copolymer and PIB in a mass ratio of 19:7. "Rubber/ polyester fabric" in Table 3 refers to a polyester fabric coated with a rubber composition. The PU film (water vapor transmission rate: 786 g/m²·24 hours) in the patch of Example 16 and the PU film (water vapor transmission rate: 8408 g/m²·24 hours) in the patches of Examples 17, 19 and 20 are "3M CoTran 9701 Backing" and "3M CoTran 9700" from 3M Company, respectively.

Patches of Examples 16 to 19 and Comparative Examples 4 and 5 were evaluated for the adhesiveness after 24 hours. The results are shown in Table 3. In addition, the patches of these Examples and Comparative Examples were placed in an incubator at 30° C. and 65% RH with a backing layer facing upward, and stored. After 24 hours, the DMSO concentration (% by mass) in the adhesive layer was quantified by GC and the change in the DMSO concentration was examined. The results are shown in Table 3. The patches of Examples 16 to 19 each having a backing layer with the water vapor transmission rate of 400 g/m$^2$·24 hours or more were good in adhesiveness after worn for 24 hours.

TABLE 3

|  |  | Example 16 | Example 17 | Example 18 | Comparative Example 4 | Example 19 | Comparative Example 5 |
|---|---|---|---|---|---|---|---|
| Adhesive layer | diclofenac sodium | 5.0 | 5.0 | 5.0 | 5.0 | 5.0 | 5.0 |
|  | Rubber adhesive (SIS/PIB = 19/7) | 32.6 | 32.6 | 32.6 | 31.5 | 31.5 | 29.2 |
|  | Tackifier resin | 32.3 | 32.3 | 32.3 | 31.2 | 31.2 | 28.9 |
|  | Liquid paraffin | 15.0 | 15.0 | 15.0 | 14.5 | 14.5 | 13.4 |
|  | DMSO | 8.0 | 8.0 | 8.0 | 10.9 | 10.9 | 16.6 |
|  | Citric acid | 2.0 | 2.0 | 2.0 | 2.0 | 2.0 | 2.0 |
|  | Oleic acid | 5.0 | 5.0 | 5.0 | 5.0 | 5.0 | 5.0 |
|  | Mesylic acid | 0 | 0 | 0 | 0 | 0 | 0 |
|  | Total (% by mass) | 100 | 100 | 100 | 100 | 100 | 100 |
| Backing layer | Material | PU film | PU nonwoven fabric | Rubber/ polyester fabric | PET film | PU nonwoven fabric | PET film |
|  | Water vapor transmission rate (g/m$^2$ · 24 h) | 786 | 8408 | 422 | 27 | 8408 | 27 |
| Results | Probe tack value just before applied (gF) | 53 | 68 | 44 | 41 | 61 | 29 |
|  | Adhesiveness after 24 hours of wear | A | A | A | B | A | B |
|  | DMSO concentration after 24 hours (vs. initial concentration %) | 3 | 3 | 10 | 98 | 12 | 90 |
|  | DMSO concentration after 24 hours (% by mass) | 0.2 | 0.2 | 0.8 | 10.7 | 1.3 | 15.0 |
|  | Rate of decrease in DMSO concentration (% by mass/h) | 0.325 | 0.325 | 0.300 | 0.008 | 0.400 | 0.067 |
|  | Half-life of DMSO concentration (h) | 4 | 4 | 7 | 1049 | 8 | 163 |

The invention claimed is:

1. A patch comprising:
   a backing layer;
   an adhesive layer laminated on the backing layer,
   wherein the backing layer is a monolayer,
   wherein a water vapor transmission rate of the backing layer is 2077 g/m$^2$·24 hours or more, the adhesive layer comprises a drug, dimethylsulfoxide (DMSO), and an adhesive,
   wherein the DMSO initial concentration % is 2 to 12 mass %, based on the total mass of the adhesive layer, and
   wherein the backing layer comprises one or more materials selected from the group consisting of a polyester, a polyurethane, a polyolefin, a polyamide and a cellulose.

2. The patch according to claim 1, wherein the water vapor transmission rate of the backing layer is 4000 g/m$^2$·24 hours or more.

3. The patch according to claim 1, wherein the water vapor transmission rate of the backing layer is 5500 g/m$^2$·24 hours or more.

4. The patch according to claim 1, wherein the adhesive layer comprises at least one adhesive selected from the group consisting of a rubber adhesive, an acrylic adhesive and a silicone adhesive.

5. The patch according to claim 1, wherein the adhesive layer comprises a styrene-isoprene-styrene block copolymer.

6. The patch according to claim 1, wherein the drug is one or more drugs selected from the group consisting of ketoprofen, diclofenac sodium and indomethacin.

7. The patch according to claim 6, wherein the adhesive layer further comprises an organic acid.

8. The patch according to claim 5, wherein the drug is one or more drugs selected from the group consisting of ketoprofen, diclofenac sodium and indomethacin.

9. The patch according to claim 8, wherein the adhesive layer further comprises an organic acid.

10. The patch according to claim 1, wherein the DMSO initial concentration % by mass is 2% by mass to 10% by mass.

11. The patch according to claim 10, wherein the DMSO initial concentration % by mass is 2% by mass to 8% by mass.

12. A patch comprising:
    a backing layer;
    an adhesive layer laminated on the backing layer,
    wherein the backing layer is a monolayer,
    wherein a water vapor transmission rate of the backing layer is 2077 g/m$^2$·24 hours or more,
    the adhesive layer comprises a drug, dimethylsulfoxide (DMSO), and an adhesive, and
    wherein a DMSO concentration % by mass after 24 hours of wear, vs. the initial DMSO concentration %, is 3 to 12, and wherein the backing layer comprises one or more materials selected from the group consisting of a polyester, a polyurethane, polyolefin, a polyamide and a cellulose.

13. The patch according to claim 1, wherein the backing layer comprises one or more materials selected from the group consisting of a knit fabric made of polyethylene terephthalate (PET), a nonwoven fabric made of PET fibers, and a polyester fabric.

14. The patch according to claim 13, wherein the backing layer comprises one or more materials selected from the group consisting of a knit fabric made of polyethylene terephthalate (PET), a nonwoven fabric made of PET fibers, and a polyester fabric.

* * * * *

UNITED STATES PATENT AND TRADEMARK OFFICE
CERTIFICATE OF CORRECTION

PATENT NO. : 12,178,922 B2
APPLICATION NO. : 17/244552
DATED : December 31, 2024
INVENTOR(S) : Tanaka et al.

It is certified that error appears in the above-identified patent and that said Letters Patent is hereby corrected as shown below:

In the Claims

Claim 14, Column 13, Line 9, please delete the phrase "according to claim 13" and replace with "according to claim 12".

Signed and Sealed this
Twenty-fifth Day of March, 2025

Coke Morgan Stewart
*Acting Director of the United States Patent and Trademark Office*